United States Patent
Greenblatt et al.

(10) Patent No.: US 7,067,518 B2
(45) Date of Patent: Jun. 27, 2006

(54) PYRIDINYL-METHYL-ETHYL CYCLOHEXANECARBOXAMIDES AS SEROTONERGIC AGENTS

(75) Inventors: Lynne P. Greenblatt, Lambertville, NJ (US); Michael G. Kelly, Thousand Oaks, CA (US); Yvette L. Palmer, Yardley, PA (US)

(73) Assignee: Wyeth, Madison, NJ (US)

( * ) Notice: Subject to any disclaimer, the term of this patent is extended or adjusted under 35 U.S.C. 154(b) by 148 days.

(21) Appl. No.: 10/652,420

(22) Filed: Aug. 29, 2003

(65) Prior Publication Data

US 2005/0107395 A1 May 19, 2005

Related U.S. Application Data

(60) Provisional application No. 60/408,356, filed on Sep. 5, 2002.

(51) Int. Cl.
*A61K 31/496* (2006.01)
*C07D 401/06* (2006.01)
*C07D 401/14* (2006.01)
*C07D 405/14* (2006.01)

(52) U.S. Cl. .......................... 514/253.01; 514/253.09; 514/253.11; 544/360; 544/364

(58) Field of Classification Search ................ 544/360, 544/364; 514/253.01, 253.09, 253.11
See application file for complete search history.

(56) References Cited

U.S. PATENT DOCUMENTS

| | | | |
|---|---|---|---|
| 3,717,634 A | 2/1973 | Wu et al. ............ | 260/256.4 N |
| 4,873,331 A | 10/1989 | Childers, Jr. et al. ....... | 544/295 |
| 4,882,432 A | 11/1989 | Abou-Gharbia et al. .... | 544/295 |
| 4,988,814 A | 1/1991 | Abou-Gharbia et al. .... | 544/295 |
| 5,340,812 A | 8/1994 | Cliffe ......................... | 514/255 |
| 5,486,518 A | 1/1996 | Yardley et al. ............. | 514/254 |
| 5,519,025 A | 5/1996 | Yardley et al. ............. | 514/254 |

FOREIGN PATENT DOCUMENTS

| | | |
|---|---|---|
| EP | 0 395313 B1 | 10/1990 |
| WO | WO 99/65887 | 12/1999 |
| WO | WO 00/35874 | 6/2000 |
| WO | WO 00/51999 | 9/2000 |
| WO | WO 00/52002 | 9/2000 |

OTHER PUBLICATIONS

Jones et al. Pharmacology, Biochemistry and Behavior, vol. 71, p. 555-568 (2002).*
Rasmussen, et al., "Section 1. Central nervous system diseases; Chap. 1. Recent Progress in Serotonin $(5-HT)_{1A}$ Receptor Modulators," in *Annual Reports in Medicinal Chemistry*, 1995, Bristol, J.A. (Ed.), 30, 1-9.
Zgombick, J.M., et al., "Pharmacological characterizations of recombinant human $5-TH_{1D\alpha}$ receptor subtypes coupled to adenylate cyclase inhibition in clonal cell lines: apparent differences in drug intrinsic efficacies between human $5-HT_{1D}$ subtypes," *Naunyn-Schmiederberg's Arch Pharmacol*, 1996, 354, 226-236.

* cited by examiner

*Primary Examiner*—Emily Bernhardt
(74) *Attorney, Agent, or Firm*—Woodcock Washburn LLP

(57) ABSTRACT

A compound having $5-HT_{1A}$ receptor activity, represented by the chemical formula

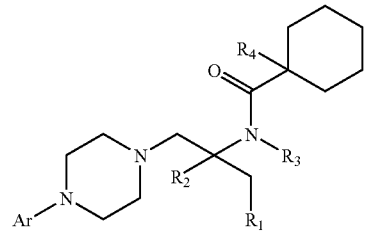

wherein:
Ar is 2-methoxyphenyl, 1H-indol-4-yl or 2,3-dihydro-1,4-benzodioxin-5-yl;
$R_1$ is 2-, 3- or 4-pyridyl;
$R_2$ is H or $C_{1-6}$alkyl;
$R_3$ is H or $C_{1-6}$alkyl; and
$R_4$ is H or methyl,
or an optical isomer thereof,
or a pharmaceutically acceptable salt of such a compound or optical isomer.

The invention also includes compositions containing such a compound, as well as methods for using a compound of the invention.

11 Claims, No Drawings

PYRIDINYL-METHYL-ETHYL CYCLOHEXANECARBOXAMIDES AS SEROTONERGIC AGENTS

This application claims the benefit of U.S. Provisional Application Ser. No. 60/408,356 filed Sep. 5, 2002.

BACKGROUND OF THE INVENTION

Compounds having selective partial agonist activity at the 5-$HT_{1A}$ receptor have established a presence in the marketplace as effective anxiolytic agents (e.g., buspirone, Buspar®, U.S. Pat. No. 3,717,634). 5-$HT_{1A}$ agonists and antagonists may find use in the treatment of several diseases such as anxiety, depression, schizophrenia, cognitive deficits resulting from neurodegenerative diseases like Alzheimer's Disease, nausea and vomiting, and in the treatment of prostate cancer (for recent references, see: K. Rasmussen and V. P. Rocco, *Recent Progress in Serotonin (5-HT)$_{1A}$ Receptor Modulators*, in Annual Reports in Medicinal Chemistry, Volume 30, J. A. Bristol, ed., pp. 1–9 (1995)).

Compounds which are active at the 5$HT_{1A}$ receptor have been disclosed in U.S. Pat. Nos. 4,873,331, 4,882,432, 4,988,814, 5,340,812, 5,486,518, and 5,519,025, in European Patent 395,313, and in PCT applications published as WO 00/52002, WO 00/35874, WO 00/51999, and WO 99/65887.

SUMMARY OF THE INVENTION

The present invention comprises a compound of formula I

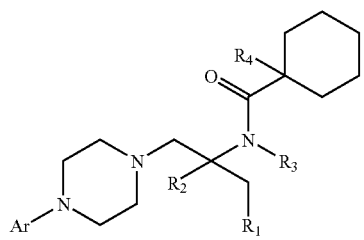

I wherein:
Ar is 2-methoxyphenyl, 1H-indol-4-yl or 2,3-dihydro-1,4-benzodioxin-5-yl;

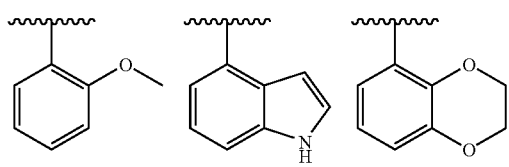

$R_1$ is 2-, 3- or 4-pyridyl;
$R_2$ is H or $C_{1-6}$ alkyl;
$R_3$ is H or $C_{1-6}$ alkyl; and
$R_4$ is H or $C_{1-6}$ alkyl,
or an optical isomer thereof,
or a pharmaceutically acceptable salt of said compound or optical isomer thereof.

The invention further comprises compositions containing a compound of formula I, and methods for using such a compound.

Various advantages of the present invention will be clear to those skilled in the art from the following description and claims.

DETAILED DESCRIPTION

A preferred embodiment of the present invention comprises compounds of formula I wherein $R_2$ is H; $R_3$ is H, methyl or ethyl; $R_4$ is H or methyl; or a pharmaceutically acceptable salt thereof. Especially preferred are compounds in the R configuration.

Optical isomers of the invention compounds can be selectively synthesized or separated using conventional procedures known to those skilled in the art of organic synthesis.

The pharmaceutically acceptable salts of the compounds of this invention include the conventional acid addition salts which are formed using a pharmaceutically acceptable organic or inorganic acid. The acid addition salts include, but are not limited to, acetate, adipate, alginate, aspartate, benzoate, benzenesulfonate, bisulfate, butyrate, citrate, camphorate, camphorsulfonate, dodecylsulfate, ethanesulfonate, fumarate, glycerophosphate, phosphate, hemisulfate, hydrochloride, hydrobromide, hydroiodide, lactate, maleate, methanesulfonate, nicotinate, oxalate, pamoate, pectinate, pivalate, propionate, succinate, tartrate, and tosylate. Furthermore, the basic nitrogen-containing groups may be quaternized with such agents as lower alkyl halides, dialkyl sulfates, long chain halides such as lauryl bromide, aralkyl halides like benzyl and phenethyl bromides.

Compounds of the present invention in which $R_3$ is hydrogen may be synthesized in four steps according to Scheme 1, starting from the appropriate amino acid which has been protected on the nitrogen atom with the t-butoxycarbonyl group (BOC). This material is coupled to the appropriately substituted aryl piperazine using a carbodiimide coupling reagent such as 1-(3-dimethylaminopropyl)-3-ethylcarbodiimide (DAEC), to afford compound 1. Removal of the BOC group under acidic conditions affords compound 2, which is reduced using a borane complex to give the penultimate intermediate 3. Subsequent acylation of 3 with the appropriate acid chloride gives compound 4, which is isolated as an acceptable salt.

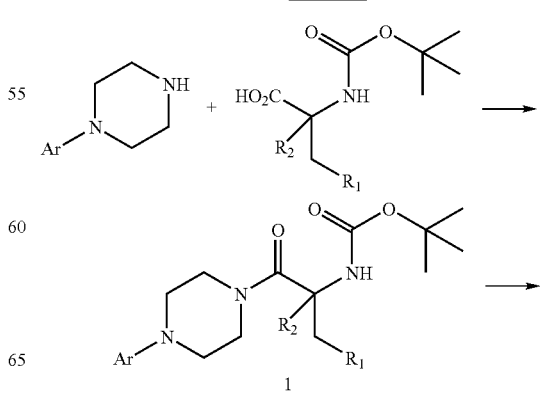

Scheme 1.

-continued

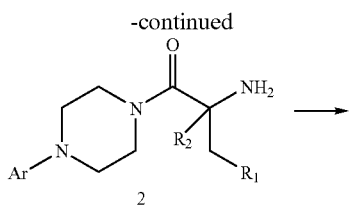

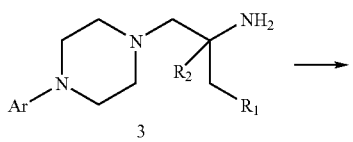

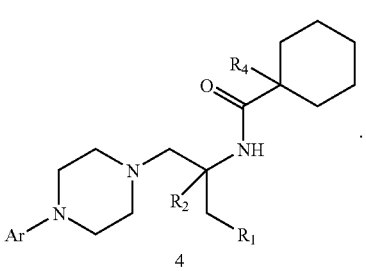

Compounds of the present invention in which $R_3$ is other than hydrogen are prepared using the method described in Scheme 2. Compound 2 is formylated or acylated to afford compound 5, which is reduced with a borane complex to afford the secondary amine 6. Subsequent acylation using the appropriate acid chloride yields the title compound 7.

Scheme 2.

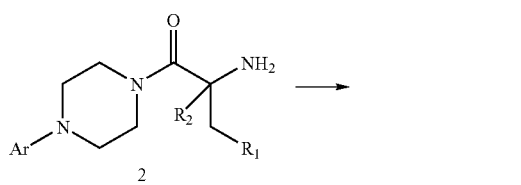

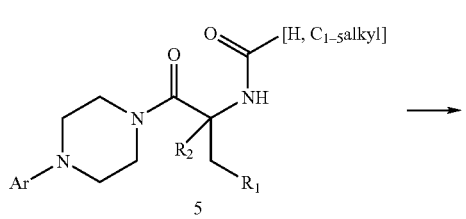

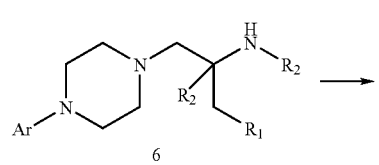

-continued

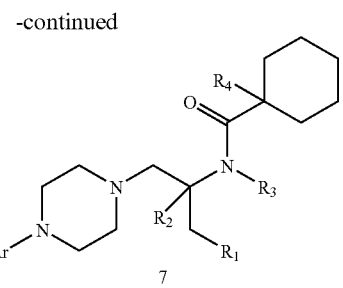

Other synthetic procedures for preparing compounds of the present invention will be apparent to those skilled in the art of organic synthesis. The compounds of this invention may prepared by conventional methods which are well known to those skilled in the art, using chemicals that are either commercially available or readily prepared following standard literature procedures.

The following examples are presented to illustrate certain embodiments of the present invention, but should not be construed as limiting the scope of this invention.

EXAMPLE 1

(R)-{2-[4-(2-Methoxy-phenyl)-piperazin-1-yl]-2-oxo-1-pyridin-3-ylmethyl-ethyl}-carbamic acid tert-butyl ester

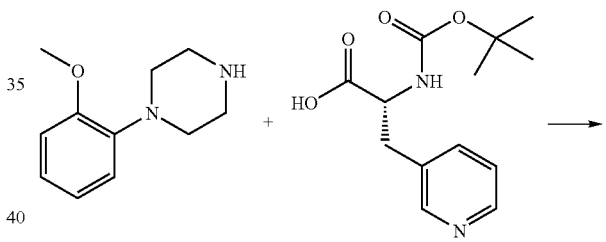

Under an inert atmosphere, to a mixture of N-t-butoxy-carbonyl-D-3-(3-pyridyl)alanine (2.0 g; 7.5 mmol), 1-(3-dimethylaminopropyl)-3-ethylcarbodiimide hydrochloride (1.44 g.; 7.5 mmol) and 1-hydroxybenzotriazole (1.32 g.; 9.8 mmol) in DMF (14 mL) at 0° C. was added 2-methoxyphenylpiperazine (1.59 g.; 8.3 mmol) and N-methylmorpholine (1.24 mL; 11.3 mmol). The reaction mixture was allowed to warm to ambient temperature, stirred at ambient temperature for 2 hours. The mixture was poured into water (30 mL), and the product extracted into ether. The organic layer was washed with saturated aqueous $NaHCO_3$ and brine, dried over $Na_2SO_4$, filtered, and the solvent removed in vacuo to afford the title compound (3.18 g., 96%) as a white amorphous solid, m.p. 142° C.; MS EI M+ @ m/z 440; ¹H NMR, 400 MHz, DMSO-d6. Analysis for $C_{24}H_{32}N_4O_4$ Calculated: C, 65.43; H, 7.32; N, 12.72 Found: C, 65.22; H, 7.33; N, 12.6.

EXAMPLE 2

(2R)-2-Amino-1-[4-(2-methoxy-phenyl)-piperazin-1-yl]-3-pyridin-3-yl-propan-1-one

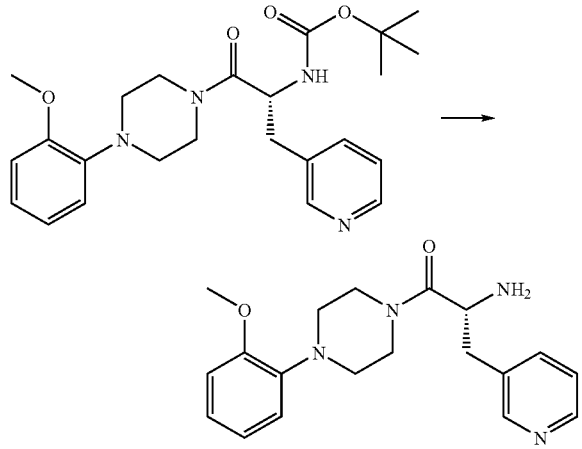

To a solution of (R)-{2-[4-(2-Methoxy-phenyl)-piperazin-1-yl]-2-oxo-1-pyridin-3-ylmethyl-ethyl}-carbamic acid tert-butyl ester (7.54 g.; 17.1 mmol) from Example 1 in THF (60 mL) at 0° C. was added HCl (4M/Dioxane) (70 mL; 0.28 mol). The mixture was stirred at ambient temperature for 3 hours, and the solvent removed in vacuo. A small portion of the trihydrochloride residue was retained for analytical purposes. The remainder of the residue was dissolved in water (70 mL), washed with ether (40 mL), and the ether layer discarded. The aqueous layer was rendered basic (pH 9–10) with saturated aqueous $Na_2CO_3$, and the product extracted into dichloromethane (3×60 mL). The combined dichloromethane layers were washed with brine, dried over MgSO4, filtered, and the solvent removed in vacuo to afford the free base of the title compound as a clear oil (5.8 g., 100%). The analytical sample as the trihydrochloride salt was recrystallized from ethanol/ether to afford a white crystalline powder, m.p. >240° C.; MS (+) ESI, [M+H]+ @ m/z 341; ¹H NMR, 400 MHz, DMSO-d6. Analysis for $C_{19}H_{24}N_4O_2 \cdot 3HCl$ Calculated: C, 50.73; H, 6.05; N, 12.46 Found: C, 50.89; H, 6.03; N, 12.41.

EXAMPLE 3

(1R)-2-[4-(2-Methoxy-phenyl)-piperazin-1-yl]-1-pyridin-3-ylmethyl-ethylamine

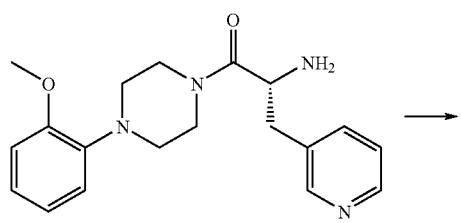

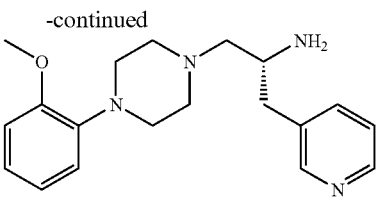

To a solution of (2R)-2-Amino-1-[4-(2-methoxy-phenyl)-piperazin-1-yl]-3-pyridin-3-yl-propan-1-one (6.23 g; 18.3 mmol, from Example 2) in THF (60 mL) was added, dropwise, $BH_3 \cdot THF$ (1.0M/THF) (73 mL; 73 mmol). The mixture was stirred at reflux for 2.5 hours, then allowed to stir at ambient temperature overnight. The mixture was cooled to 0–5° C., cautiously treated with 5M HCl (30 mL), stirred at ambient temperature for 4 hours. The mixture was then concentrated on a rotary evaporator to remove THF, diluted with water (30 mL), and the pH adjusted to 10 with concentrated ammonium hydroxide. The product was extracted into ethyl acetate (3×50 mL). The combined organic layers were washed with brine, dried over MgSO4, filtered, and the solvent removed in vacuo to yield the title compound as a free base (5.24 g.; 88%). The analytical sample was converted to the hydrochloride salt with ethereal HCl to yield a white crystalline solid, m.p. 168–169° C.; MS (+) ESI, [M+H]+ @ m/z 327; 1H NMR, 400 MHz, DMSO-d6. Analysis for $C_{19}H_{26}N_4O \cdot HCl \cdot H_2O \cdot 0.25\ C_2H_6O$ Calculated: C, 62.21; H, 8.16; N, 14.88 Found: C, 61.72; H, 7.65; N, 14.17.

EXAMPLE 4

(R)-Cyclohexanecarboxylic acid {2-[4-(2-methoxy-phenyl)-piperazin-1-yl]-1-pyridin-3-ylmethyl-ethyl}-amide

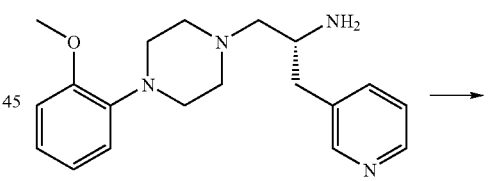

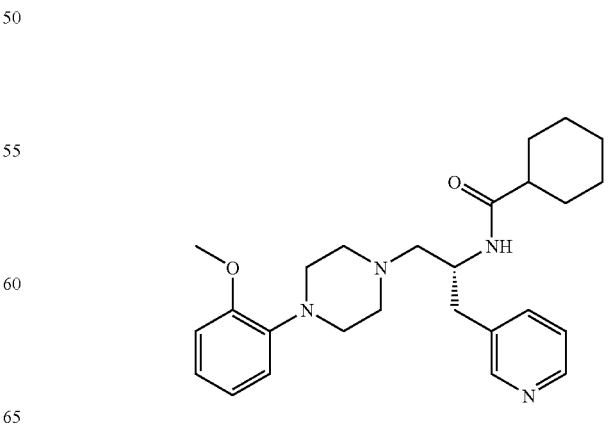

To a solution of (1R)-2-[4-(2-Methoxy-phenyl)-piperazin-1-yl]-1-pyridin-3-ylmethyl-ethylamine (162 mg.; 0.5 mmol, from Example 3) in dichloromethane (5 mL) at 0° C. was added triethylamine (0.14 mL; 1.0 mmol) and cyclohexanecarbonyl chloride (0.07 mL; 0.55 mmol). The reaction mixture was stirred while allowing to warm to ambient temperature over 1 hour. The mixture was washed with saturated NaHCO$_3$ (5 mL), dried over MgSO$_4$, filtered, and the solvent removed in vacuo. The crude residue was purified by flash chromatography on silica gel (5% methanol/chloroform) to afford the free base of the title compound as a clear oil (205 mg; 94%). Treatment with an equimolar amount of maleic acid in ethanol yielded the maleate salt as a white amorphous solid, m.p. 112–115° C.; MS (+) FAB [M+H]$^+$ @ m/z 437, [M+Na]$^+$ @ m/z 459; $^1$H NMR, 400 MHz, DMSO-d$_6$. Analysis for C$_{26}$H$_{36}$N$_4$O$_2$·C$_4$H$_4$O$_4$·H2O Calculated: C, 63.14; H, 7.42; N, 9.82 Found: C, 63.39; H, 7.21; N, 9.64.

EXAMPLE 5

(R)-1-Methyl-cyclohexanecarboxylic acid {2-[4-(2-methoxy-phenyl)-piperazin-1-yl]-1-pyridin-3-ylmethyl-ethyl}-amide

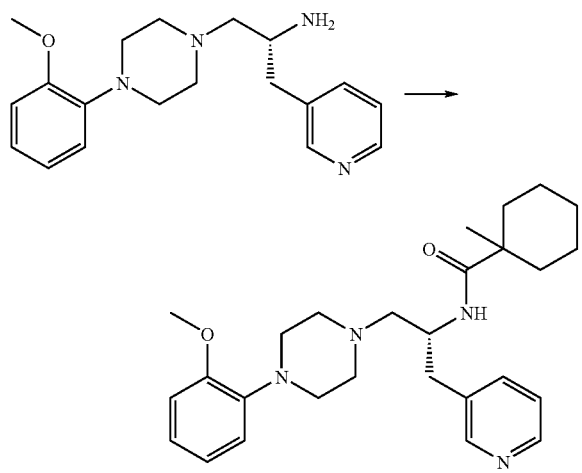

To a solution of (1R)-2-[4-(2-Methoxy-phenyl)-piperazin-1-yl]-1-pyridin-3-ylmethyl-ethylamine (326 mg.; 1 mmol, from Example 3) in dichloromethane (15 mL) at 0° C. was added triethylamine (0.28 mL; 2 mmol) and 1-methyl-1-cyclohexanecarbonyl chloride (160 mg.; 1 mmol). The reaction mixture was stirred while allowing to warm to ambient temperature over 1 hour, washed sequentially with saturated aqueous NaHCO$_3$ and brine, dried over MgSO$_4$, filtered, and the solvent removed in vacuo. The crude residue was purified by flash chromatography on silica gel (5% methanol/chloroform) to yield the free base of the title compound as a clear oil (132 mg.; 29%). Treatment with an equimolar amount of fumaric acid in ethanol afforded the fumarate salt as an off-white amorphous solid, m.p. 150–152° C.; MS (+) FAB, [M+H]$^+$ @ m/z 451, [M+Na]$^+$ @ m/z 473; $^1$H NMR, 400 MHz, DMSO-d$_6$. Analysis for C$_{27}$H$_{38}$N$_4$O$_2$·C$_4$H$_4$O$_4$·0.5H$_2$O Calculated: C, 64.68; H, 7.53; N, 9.73 Found: C, 64.89; H, 7.18; N, 9.64.

EXAMPLE 6

(R)-{2-[4-(2-Methoxy-phenyl)-piperazin-1-yl]-2-oxo-1-pyridin-4-ylmethyl-ethyl}-carbamic acid tert-butyl ester

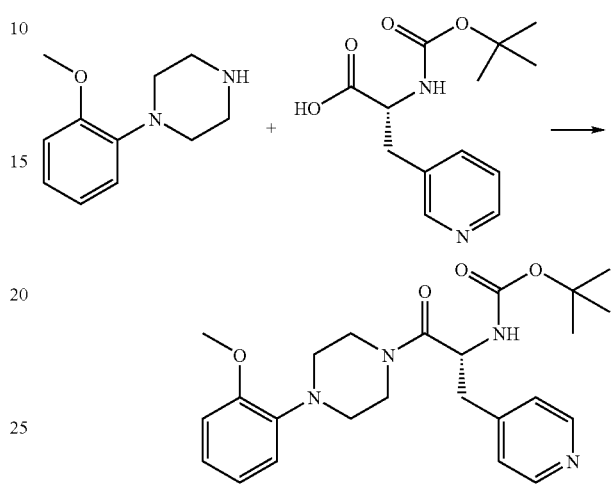

Under an inert atmosphere, to a mixture of N-t-butoxycarbonyl-D-3-(4-pyridyl)alanine (2.0 g; 7.5 mmol), 1-(3-dimethylaminopropyl)-3-ethylcarbodiimide hydrochloride (1.44 g.; 7.5 mmol) and 1-hydroxybenzotriazole (1.32 g.; 9.8 mmol) in DMF (14 mL) at 0° C. was added 2-methoxyphenylpiperazine (1.59 g.; 8.3 mmol) and N-methylmorpholine (1.24 mL; 11.3 mmol). The reaction mixture was allowed to warm to ambient temperature, stirred at ambient temperature for 2 hours. The mixture was poured into water (30 mL), and the product extracted into ether. The organic layer was washed with saturated aqueous NaHCO$_3$ and brine, dried over Na$_2$SO$_4$, filtered, and the solvent removed in vacuo to afford the title compound (3.16 g., 96%) as a white amorphous solid, m.p. 105° C., MS (+) FAB [M+H]$^+$ @ m/z 441, [M+Na]$^+$ @ m/z 463; $^1$H NMR (400 MHz, DMSO-d$_6$). Analysis for C$_{24}$H$_{32}$N$_4$O$_4$·0.5H$_2$O Calculated: C, 64.12; H, 7.40; N, 12.46 Found: C, 64.36; H, 7.31; N, 12.58.

EXAMPLE 7

(2R)-2-Amino-1-[4-(2-methoxy-phenyl)-piperazin-1-yl]-3-pyridin-4-yl-propan-1-one

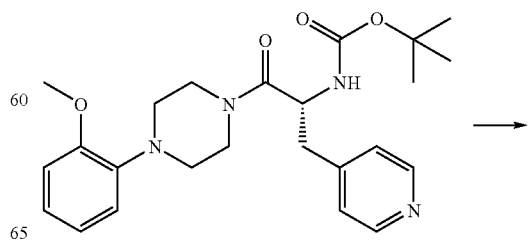

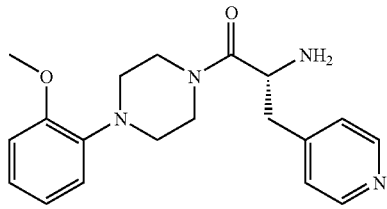

To a solution of (R)-{2-[4-(2-Methoxy-phenyl)-piperazin-1-yl]-2-oxo-1-pyridin-4-ylmethyl-ethyl}-carbamic acid tert-butyl ester (7.96 g.; 18 mmol) from Example 6 in THF (60 mL) at 0° C. was added HCl (4M/Dioxane) (74 mL; 0.3 mol). The mixture was stirred at ambient temperature for 3 hours, and the solvent removed in vacuo. The residue was dissolved in water (70 mL), washed with ether (40 mL). The aqueous layer was rendered basic (pH 9–10) with saturated aqueous Na$_2$CO$_3$, and the product extracted into dichloromethane (3×60 mL). The combined dichloromethane layers were washed with brine, dried over MgSO$_4$, filtered, and the solvent removed in vacuo to afford the free base of the title compound as a clear oil (6.12 g., 100%). An analytical sample was prepared by treatment with ethereal HCl to yield the hydrochloride salt as an off-white crystalline solid, m.p. >175–177° C.; MS (+) ESI, [M+H]$^+$ @ m/z 341; $^1$H NMR, 400 MHz, DMSO-d$_6$. Analysis for C$_{19}$H$_{24}$N$_4$O$_2$.1.1HCl.0.5H$_2$O Calculated: C, 58.58; H, 6.75; N, 14.38 Found: C, 58.64; H, 6.46; N, 14.25.

EXAMPLE 8

(1R)-2-[4-(2-Methoxy-phenyl)-piperazin-1-yl]-1-pyridin-4-ylmethyl-ethylamine

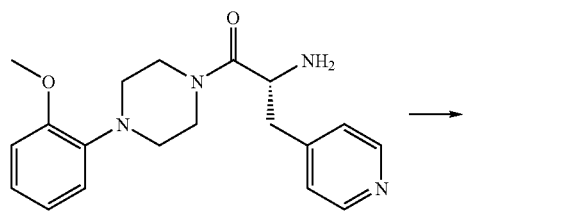

To a solution of (2R)-2-Amino-1-[4-(2-methoxy-phenyl)-piperazin-1-yl]-3-pyridin-4-yl-propan-1-one (6.18 g; 18 mmol, from Example 7) in THF (60 mL) was added, dropwise, BH$_3$.THF (1.0M/THF) (73 mL; 73 mmol). The mixture was stirred at reflux for 2 hours, cooled to ambient temperature, cautiously treated with 6N HCl (45 mL), stirred at ambient temperature for 1 hours. The mixture was then diluted with water (100 mL), concentrated on a rotary evaporator to remove THF, and the aqueous residue washed with ether (30 mL). The aqueous layer was rendered basic (pH 9–10) with concentrated NH$_4$OH, and the product extracted into dichloromethane (3×75 mL). The combined dichloromethane layers were washed with brine, dried over MgSO$_4$, filtered, and the solvent removed in vacuo to yield the title compound as a free base (4.85 g.; 82%). The analytical sample was converted to the hydrochloride salt with ethereal HCl to yield an off-white crystalline solid, m.p. 177–178° C.; MS (+) ESI, [M+H]$^+$ @ m/z 327; $^1$H NMR, 400 MHz, DMSO-d$_6$. Analysis for C$_{19}$H$_{26}$N$_4$O.HCl.0.3H$_2$O.0.3 C$_2$H$_6$O Calculated: C, 61.61; H, 7.75; N, 14.66 Found: C, 61.45; H, 7.80; N, 14.49.

EXAMPLE 9

(R)-Cyclohexanecarboxylic acid {2-[4-(2-methoxy-phenyl)-piperazin-1-yl]-1-pyridin-4-ylmethyl-ethyl}-amide

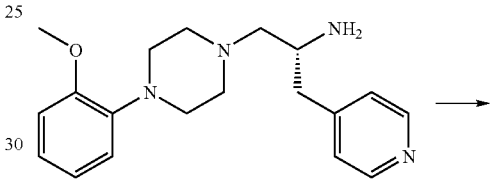

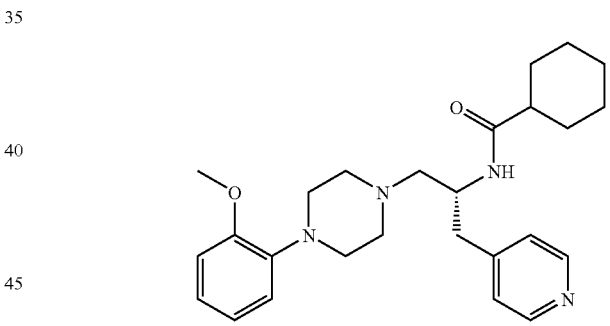

To a solution of (1R)-2-[4-(2-Methoxy-phenyl)-piperazin-1-yl]-1-pyridin-4-ylmethyl-ethylamine (800 mg.; 2.45 mmol, from Example 8) in dichloromethane (30 mL) at 0° C. was added triethylamine (0.68 mL; 4.9 mmol) and cyclohexanecarbonyl chloride (0.33 mL; 2.45 mmol). The reaction mixture was stirred while allowing to warm to ambient temperature over 1 hour. The mixture was washed with saturated NaHCO$_3$ (5 mL), dried over MgSO$_4$, filtered, and the solvent removed in vacuo. The crude residue was purified by flash chromatography on silica gel (2% methanol/chloroform) to afford the free base of the title compound as a white gummy foam (610 mg; 57%). Treatment with an equimolar amount of maleic acid in ethanol yielded the maleate salt as an off-white amorphous solid, m.p. 145–147° C.; MS (+) FAB [M+H]$^+$ @ m/z 437, [M+Na]$^+$ @ m/z 459; $^1$H NMR, 400 MHz, DMSO-d$_6$. Analysis for C$_{26}$H$_{36}$N$_4$O$_2$.C$_4$H$_4$O$_4$.0.5H$_2$O Calculated: C, 64.15; H, 7.36; N, 9.97 Found: C, 64.23; H, 7.37; N, 9.88

EXAMPLE 10

(R)-1-Methyl-cyclohexanecarboxylic acid {2-[4-(2-methoxy-phenyl)-piperazin-1-yl]-1-pyridin-4-ylmethyl-ethyl}-amide

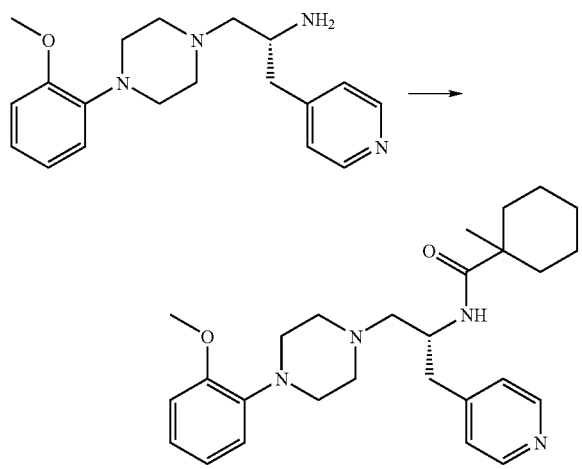

To a solution of (1R)-2-[4-(2-Methoxy-phenyl)-piperazin-1-yl]-1-pyridin-4-ylmethyl-ethylamine (726 mg.; 2.23 mmol, from Example 8) in dichloromethane (30 mL) at 0° C. was added triethylamine (0.62 mL; 4.45 mmol) and 1-methyl-1-cyclohexanecarbonyl chloride (356 mg.; 2.23 mmol). The reaction mixture was stirred while allowing to warm to ambient temperature over 1 hour, washed sequentially with saturated aqueous NaHCO₃ and brine, dried over MgSO₄, filtered, and the solvent removed in vacuo. The crude residue was purified by flash chromatography on silica gel (2% methanol/chloroform) to yield the free base of the title compound as a clear oil (695 mg.; 69%). Treatment with an equimolar amount of fumaric acid in ethanol afforded the fumarate salt as a white amorphous solid, m.p. 145° C.; MS EI M⁺ @ m/z 450; ¹H NMR, 400 MHz, DMSO-d₆. Analysis for $C_{27}H_{38}N_4O_2C_4H_4O_4 \cdot 0.5H_2O$ Calculated: C, 64.68; H, 7.53; N, 9.73 Found: C, 64.97; H, 7.53; N, 9.66

EXAMPLE 11

(R)-{2-[4-(2-Methoxy-phenyl)-piperazin-1-yl]-2-oxo-1-pyridin-2-ylmethyl-ethyl}-carbamic acid tert-butyl ester

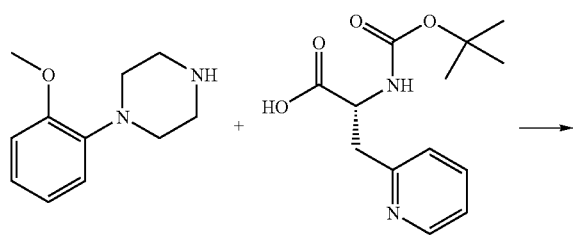

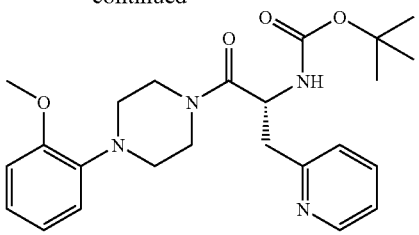

Under an inert atmosphere, to a mixture of N-t-butoxy-carbonyl-D-3-(2-pyridyl)alanine (2.0 g; 7.5 mmol), 1-(3-dimethylaminopropyl)-3-ethylcarbodiimide hydrochloride (1.44 g.; 7.5 mmol) and 1-hydroxybenzotriazole (1.32 g.; 9.8 mmol) in DMF (14 mL) at 0° C. was added 2-methoxyphenylpiperazine (1.59 g.; 8.3 mmol) and N-methylmorpholine (1.24 mL; 11.3 mmol). The reaction mixture was allowed to warm to ambient temperature, stirred at ambient temperature for 2 hours. The mixture was poured into water (40 mL), and the product extracted into ether. The organic layer was washed with saturated aqueous NaHCO₃ and brine, dried over Na₂SO₄, filtered, and the solvent removed in vacuo to afford the title compound (3.16 g., 96%) as a dark purple solid foam, MS (+) FAB [M+H]⁺ @ m/z 441, [M+Na]⁺ @ m/z 463; ¹H NMR (400 MHz, DMSO-d₆).

EXAMPLE 12

(2R)-2-Amino-1-[4-(2-methoxy-phenyl)-piperazin-1-yl]-3-pyridin-2-yl-propan-1-one

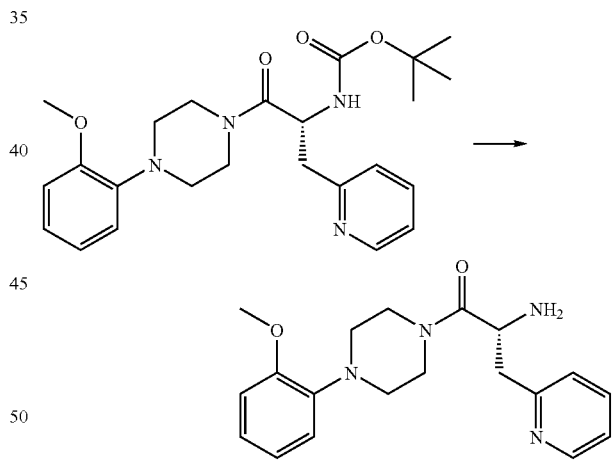

To a solution of (R)-{2-[4-(2-Methoxy-phenyl)-piperazin-1-yl]-2-oxo-1-pyridin-2-ylmethyl-ethyl}-carbamic acid tert-butyl ester (3.16 g.; 7.18 mmol from Example 11) in THF (30 mL) at 0° C. was added HCl (4M/Dioxane) (30 mL; 0.12 mol). The mixture was stirred at ambient temperature for 3 hours, and the solvent removed in vacuo. The residue was dissolved in water (35 mL), washed with ether (20 mL). The aqueous layer was rendered basic (pH 9–10) with saturated aqueous Na₂CO₃, and the product extracted into dichloromethane (3×60 mL). The combined dichloromethane layers were washed with brine, dried over MgSO₄, filtered, and the solvent removed in vacuo. The crude residue was purified by flash chromatography on silica gel (5% methanol/chloroform) to afford the free base of the title compound as a light yellow oil (2.07 g.; 85%); MS (+) FAB, [M+H]⁺ @ m/z 341, [M+Na]⁺ @ m/z 363; ¹H NMR, 400 MHz, DMSO-$d_6$.

EXAMPLE 13

(1R)-2-[4-(2-Methoxy-phenyl)-piperazin-1-yl]-1-pyridin-2-ylmethyl-ethylamine

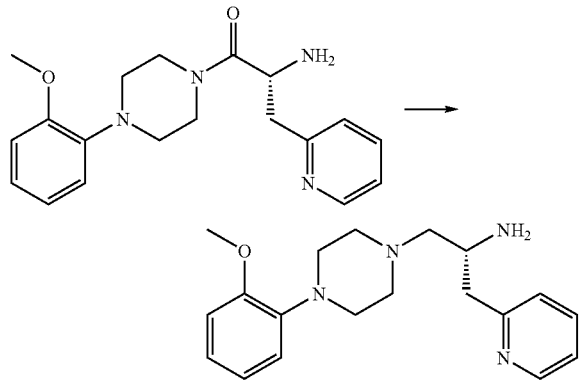

Under a nitrogen atmosphere, to a solution of (2R)-2-Amino-1-[4-(2-methoxy-phenyl)-piperazin-1-yl]-3-pyridin-2-yl-propan-1-one (1.02 g; 3 mmol, from Example 12) in THF (10 mL) was added, dropwise, BF$_3$.Et$_2$O (0.37 mL; 3 mmol). The reaction mixture was heated to reflux, BH$_3$.THF (1.0M/THF) (4.3 mL; 4.3 mmol) was added dropwise at reflux, and the mixture stirred at reflux for 2.5 hours. The mixture was cooled to 0–5° C., cautiously treated with 3N HCl (10 mL), stirred at ambient temperature for 1 hour. The mixture was heated to reflux for 5 minutes, cooled to ambient temperature, concentrated on a rotary evaporator to remove THF. The aqueous residue was washed with ether (5 mL), and the ether layer discarded. The aqueous layer was rendered basic (pH 9–10) with 2.5N NaOH, and the product extracted into ethyl acetate (25 mL). The organic layer was washed with brine, dried over MgSO$_4$, filtered, and the solvent removed in vacuo to yield the free base of the title compound as an amber oil (804 mg; 82%), MS EI, M⁺ @ m/z 326; ¹H NMR, 400 MHz, DMSO-$d_6$.

EXAMPLE 14

(R)-Cyclohexanecarboxylic acid {2-[4-(2-methoxy-phenyl)-piperazin-1-yl]-1-pyridin-2-ylmethyl-ethyl}-amide

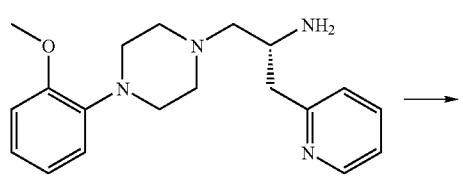

-continued

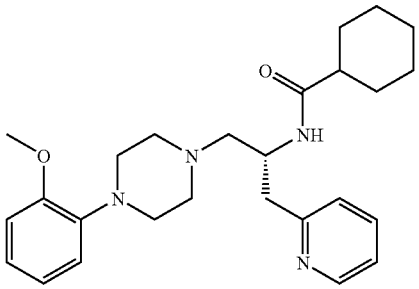

To a solution of (1R)-2-[4-(2-Methoxy-phenyl)-piperazin-1-yl]-1-pyridin-2-ylmethyl-ethylamine (780 mg.; 2.4 mmol, from Example 13) in dichloromethane (30 mL) at 0° C. was added triethylamine (0.67 mL; 4.8 mmol) and a solution of cyclohexanecarbonyl chloride (0.33 mL; 2.45 mmol) in dichloromethane (5 mL). The reaction mixture was stirred while allowing to warm to ambient temperature over 1 hour. The mixture was washed with saturated NaHCO$_3$ (15 mL), dried over MgSO$_4$, filtered, and the solvent removed in vacuo. The crude residue was purified by flash chromatography on silica gel (2% methanol/chloroform) to afford the free base of the title compound as a white gummy foam (750 mg; 72%). Treatment with an equimolar amount of fumaric acid in ethanol yielded the fumarate salt as a white amorphous solid, m.p. 136–141° C.; MS (+) FAB [M+H]⁺ @ m/z 437, [M+Na]⁺ @ m/z 459; ¹H NMR, 400 MHz, DMSO-$d_6$. Analysis for $C_{26}H_{36}N_4O_2$. $C_4H_4O_4$.2H$_2$O Calculated: C, 61.21; H, 7.53; N, 9.52 Found: C, 61.79; H, 7.27; N, 9.31

EXAMPLE 15

(R)-1-Methyl-cyclohexanecarboxylic acid {2-[4-(2-methoxy-phenyl)-piperazin-1-yl]-1-pyridin-2-ylmethyl-ethyl}-amide

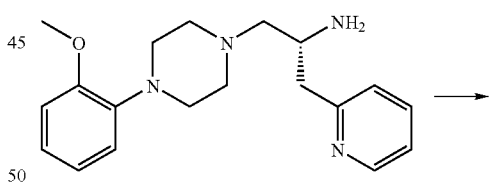

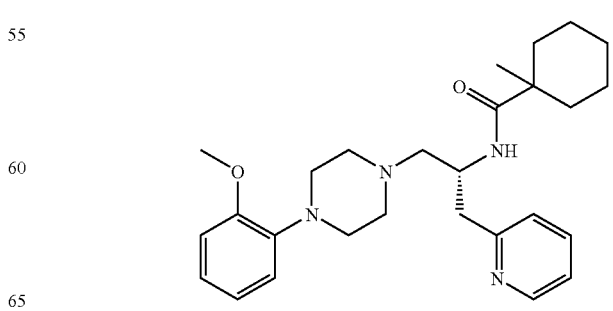

To a solution of (1R)-2-[4-(2-Methoxy-phenyl)-piperazin-1-yl]-1-pyridin-2-ylmethyl-ethylamine (1.06.; 3.2 mmol, from Example 13) in dichloromethane (40 mL) at 0° C. was added triethylamine (0.90 mL; 6.5 mmol) and a solution of 1-methyl-1-cyclohexanecarbonyl chloride (520 mg.; 3.2 mmol) in dichloromethane (6 mL). The reaction mixture was stirred while allowing to warm to ambient temperature over 1 hour, washed sequentially with saturated aqueous NaHCO$_3$ and brine, dried over MgSO$_4$, filtered, and the solvent removed in vacuo. The crude residue was purified by flash chromatography on silica gel (2% methanol/chloroform) to yield the free base of the title compound as a clear oil (1.0 g.; 70%). Treatment with an equimolar amount of fumaric acid in ethanol afforded the fumarate salt as a white amorphous solid, m.p. 135–139° C.; MS (+) FAB [M+H]$^+$ @ m/z 451; $^1$H NMR, 400 MHz, DMSO-d$_6$. Analysis for C$_{27}$H$_{38}$N$_4$O$_2$·C$_4$H$_4$O$_4$ Calculated: C, 65.70; H, 7.47; N, 9.89 Found: C, 65.29; H, 7.69; N, 9.77

EXAMPLE 16

(2R)-1-[4-(2-Methoxy-phenyl)-piperazin-1-yl]-2-oxo-1-pyridin-3-ylmethyl-ethyl-formamide

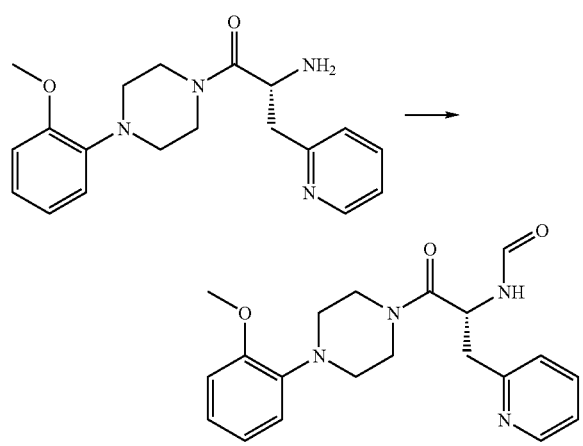

A mixture of formic acid (0.39 mL; 10.3 mmol) and acetic anhydride (0.8 mL; 8.5 mmol) was stirred at 60° C. for 4 hours, then cooled to ambient temperature. The resulting mixed anhyrdride was added to a −10° C. solution of (2R)-2-Amino-1-[4-(2-methoxy-phenyl)-piperazin-1-yl]-3-pyridin-2-yl-propan-1-one (440 mg.; 1.3 mmol, from Example 12) and triethylamine (0.18 mL; 1.3 mmol) in THF (13 mL). The reaction mixture was stirred while allowing to warm to ambient temperature, and stirred at ambient temperature overnight. The mixture was poured into aqueous saturated NaHCO$_3$ (20 mL), and the produce extracted into ethyl acetate (20 mL). The organic layer was washed with brine, dried over MgSO$_4$, filtered, and the solvent removed in vacuo. The crude residue was purified by flash chromatography on silica gel (5% methanol/chloroform) to afford the title compound as a clear oil (373 mg.; 78%). MS EI M+.@ m/z 368; $^1$H NMR, 400 MHz, DMSO-d$_6$.

EXAMPLE 17

(2R)-1-[4-(2-methoxyphenyl)piperazin-1-yl]-N-methyl-3-pyridin-2-ylpropan-2-amine

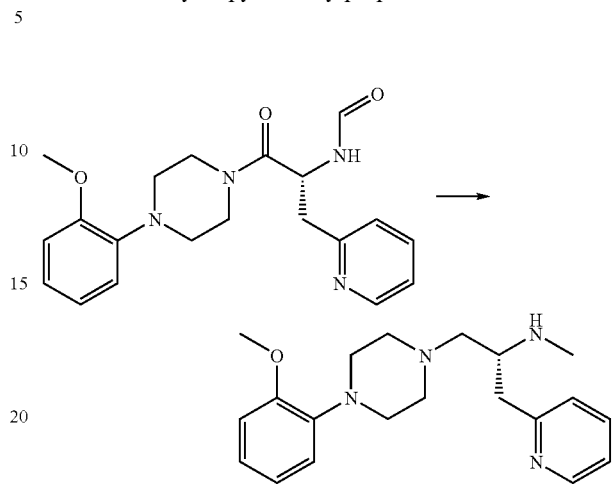

Under a nitrogen atmosphere, to a solution of (2R)-1-[4-(2-Methoxy-phenyl)-piperazin-1-yl]-2-oxo-1-pyridin-3-yl-methyl-ethyl-formamide (330 mg.; 0.9 mmol, from Example 16) in THF (4.5 mL) was added BF$_3$.Et2O (0.22 mL; 1.8 mmol). The reaction mixture was heated to reflux and treated, at reflux, with 1M BH$_3$.THF in THF (9 mL; 9 mmol). Stirring was continued at reflux for 16 hours. The reaction mixture was cooled to ambient temperature and treated dropwise with 6N aqueous HCl (10 mL). The mixture was then heated to reflux with stirring for 6 hours, allowed to cool to ambient temperature, stirred at ambient temperature for 16 hours. The mixture was concentrated on a rotary evaporator to remove THF, and the aqueous residue was rendered basic with NaHCO$_3$, extracted with ethyl acetate. The organic layer was washed with brine, dried over MgSO$_4$, filtered, and the solvent removed in vacuo to yield the free base of the title compound as an amber oil (96 mg.; 31%). MS (+) ESI [M+H]$^+$ @ m/z 341; $^1$H NMR, 300 MHz, CDCl$_3$.

EXAMPLE 18

1-Methyl-cyclohexanecarboxylic acid {(1R)-2-[4-(2-methoxy-phenyl)-piperazin-1-yl]-1-pyridin-2-ylmethyl-ethyl}-methyl-amide

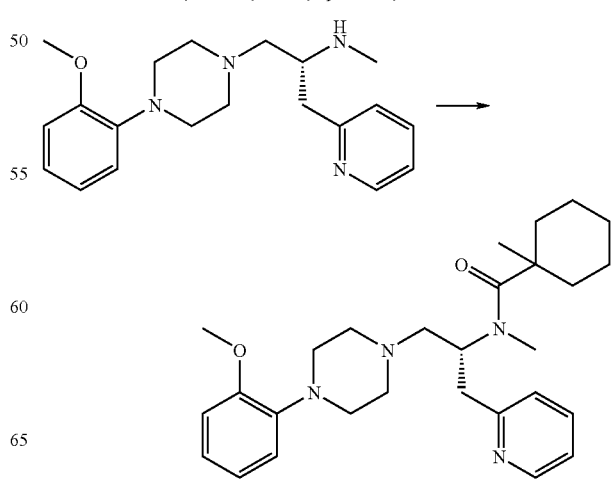

To a solution of (2R)-1-[4-(2-methoxyphenyl)piperazin-1-yl]-N-methyl-3-pyridin-2-ylpropan-2-amine (90 mg.; 0.26 mmol, from Example 17) in dichloromethane (3 mL) at 0° C. was added a solution of potassium carbonate (180 mg.; 1.3 mmol) in water (0.5 mL), followed by a solution of 1-methyl-1-cyclohexanecarbonyl chloride (41 mg.; 0.26 mmol) in dichloromethane (0.5 mL). The reaction mixture was stirred while allowing to warm to ambient temperature over 1 hour, diluted with dichloromethane (5 mL), and the layers allowed to separate. The organic layer was dried over MgSO$_4$, filtered, and the solvent removed in vacuo. The crude residue was purified by flash chromatography on silica gel (10% methanol/ethyl acetate) to yield the free base of the title compound as a clear oil (68 mg.; 56%). Treatment with an equimolar amount of fumaric acid in acetonitrile afforded the fumarate salt as a white crystalline solid, m.p. 145–146° C.; MS (+) ESI [M+H]$^+$ @ m/z 465; $^1$H NMR, 400 MHz, DMSO-d$_6$. Analysis for C$_{28}$H$_{40}$N$_4$O$_2$·C$_4$H$_4$O$_4$ Calculated: C, 66.18; H, 7.64; N, 9.65 Found: C, 65.95; H, 7.41; N, 9.54

EXAMPLE 19

(1R)-2-[4-(1H-indol-4-yl)piperazin-1-yl]-2-oxo-1-(pyridin-2-ylmethyl)ethylformamide

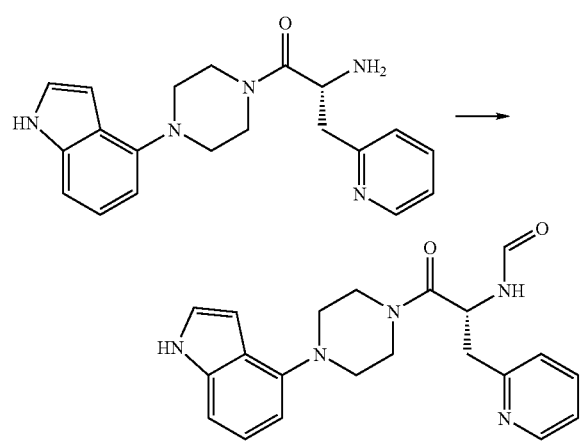

A mixture of formic acid (0.9 mL; 24 mmol) and acetic anhydride (1.8 mL; 19.5 mmol) was stirred at 60° C. for 4 hours, then cooled to ambient temperature. The resulting mixed anhydride was added to a –10° C. solution of (1R)-2-[4-(1H-indol-4-yl)piperazin-1-yl]-2-oxo-1-(pyridin-2-ylmethyl)ethylamine (prepared in two steps from 4-piperazin-1-yl-1H-indole and (2R)-2-[(tert-butoxycarbonyl)amino]-3-pyridin-2-ylpropanoic acid according to the procedures outlined in examples 1 and 2) (1.07 g.; 3.0 mmol) in THF (30 mL). The mixture was allowed to warm to ambient temperature over 3 hours, diluted with ethyl acetate, and washed with saturated aqueous Na$_2$CO$_3$. The organic layer was dried over MgSO$_4$, filtered, and the solvent removed in vacuo. The crude residue was purified by flash chromatography to afford the title compound as a beige solid foam (720 mg.; 64%). MS EI M$^+$.@ m/z 377; $^1$H NMR, 400 MHz, DMSO-d$_6$.

EXAMPLE 20

(2R)-1-[4-(1H-indol-4-yl)piperazin-1-yl]-N-methyl-3-pyridin-2-yl propan-2-amine

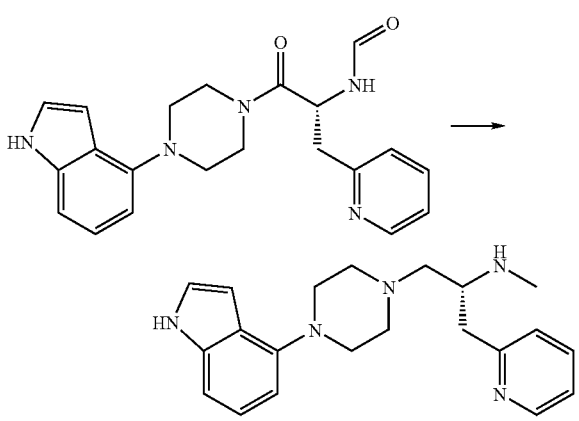

To a solution of (1R)-2-[4-(1H-indol-4-yl)piperazin-1-yl]-2-oxo-1-(pyridin-2-ylmethyl)ethylformamide (710 mg.; 1.9 mmol, from Example 19) in THF (10 mL) was added BF$_3$·Et$_2$O (0.47 mL; 3.8 mmol). The reaction mixture was heated to reflux, and treated, at reflux, with a 1M solution of BH$_3$·THF in THF (19 mL; 19 mmol). Stirring was continued at reflux for 16 hours. The mixture was cooled to ambient temperature, cautiously treated with 5N aqueous HCl (20 mL), and heated to reflux for 4 hours. The mixture was cooled to ambient temperature and concentrated in vacuo to remove THF. The aqueous residue was washed with ether, and the ether layer discarded. The aqueous layer was rendered basic with 6N NaOH, and extracted with dichloromethane. The organic layer was dried over MgSO$_4$, filtered, and the solvent removed in vacuo to afford the title compound as a white solid (110 mg.; 17%). MS (+) ESI [M+H]$^+$ @ m/z 350.

EXAMPLE 21

1-Methyl-cyclohexanecarboxylic acid {(1R)-2-[4-(1H-indol-4-yl)piperazin-1-yl]-1-pyridin-2-ylmethyl-ethyl}-methyl-amide

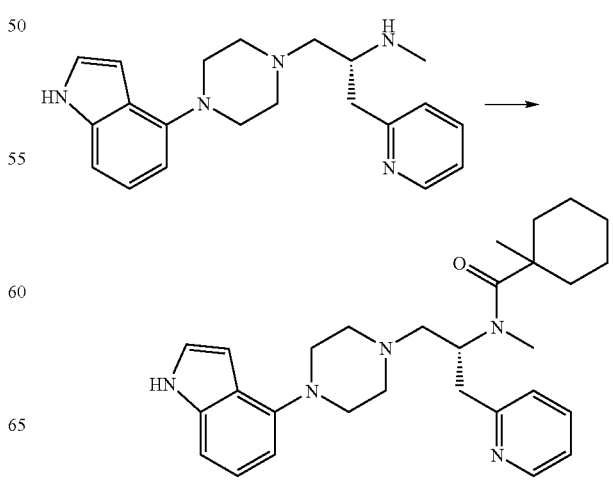

To a solution of (2R)-1-[4-(1H-indol-4-yl)piperazin-1-yl]-N-methyl-3-pyridin-2-ylpropan-2-amine (349 mg.; 1 mmol, from Example 20) in dichloromethane (10 mL) at 0° C. is added a solution of potassium carbonate (690 mg.; 5 mmol) in water (1.6 mL), followed by a solution of 1-methyl-1-cyclohexanecarbonyl chloride (160 mg.; 1 mmol) in dichloromethane (1.6 mL). The reaction mixture is stirred while allowing to warm to ambient temperature over 1 hour, diluted with dichloromethane (20 mL), and the layers allowed to separate. The organic layer is dried over MgSO$_4$, filtered, and the solvent removed in vacuo. The crude residue is purified by flash chromatography on silica gel (10% methanol/ethyl acetate) to yield the free base of the title compound. The fumarate salt is prepared by treatment with an equimolar amount of fumaric acid in ethanol.

EXAMPLE 22

1-Methyl-cyclohexanecarboxylic acid {(1R)-2-[4-(2,3-dihydro-benzo[1,4]dioxin-5-yl)-piperazin-1-yl]-1-pyridin-3-ylmethyl-ethyl}-amide

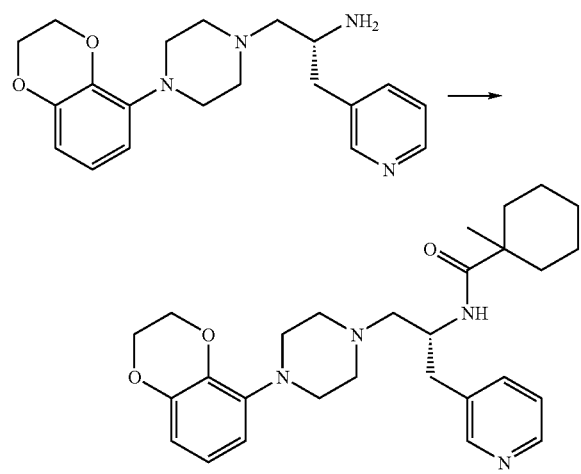

To a solution of (2R)-1-[4-(2,3-dihydro-1,4-benzodioxin-5-yl)piperazin-1-yl]-3-pyridin-3-ylpropan-2-amine (prepared in 3 steps from 1-(2,3-dihydro-1,4-benzodioxin-5-yl)piperazine and (2R)-2-[(tert-butoxycarbonyl)amino]-3-pyridin-3-ylpropanoic acid, according to the procedures outlined in examples 1, 2 and 3) (350 mg.; 1.1 mmol) in dichloromethane (5 mL), at 0° C., was added triethylamine (0.3 mL; 2.2. mmol), followed by a solution of 1-methyl-1-cyclohexanecarbonyl chloride (170 mg.; 1.1 mmol) in dichloromethane (1 mL). The reaction mixture was stirred while allowing to warm to ambient temperature over 1 hour, washed sequentially with saturated aqueous NaHCO$_3$ and brine, dried over MgSO$_4$, filtered, and the solvent removed in vacuo. Treatment with ethanolic HCl afforded the dihydrochloride salt, m.p. 188–190° C.; MS (+) ESI [M+H]$^+$ @ m/z 479; $^1$H NMR, 400 MHz, DMSO-d$_6$. Analysis for C$_{28}$H$_{38}$N$_4$O$_3$.2HCl.1.5H$_2$O Calculated: C, 58.13; H, 7.49; N, 9.68 Found: C, 58.64; H, 7.43; N, 9.61

EXAMPLE 23

1-Methyl-cyclohexanecarboxylic acid {(1R)-2-[4-(2,3-dihydro-benzo[1,4]dioxin-5-yl)-piperazin-1-yl]-1-pyridin-4-ylmethyl-ethyl}-amide

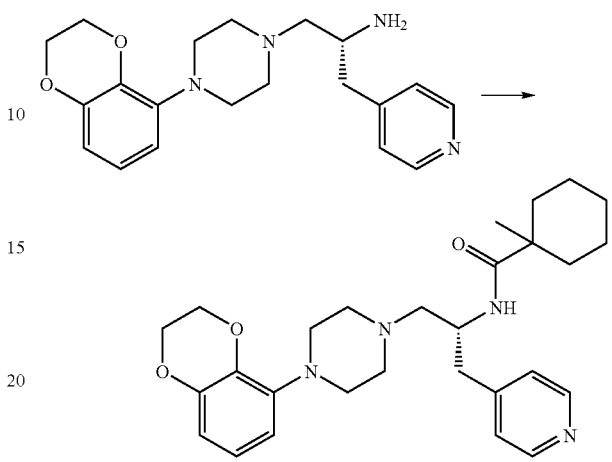

To a solution of (2R)-1-[4-(2,3-dihydro-1,4-benzodioxin-5-yl)piperazin-1-yl]-3-pyridin-4-ylpropan-2-amine (prepared in 3 steps from 1-(2,3-dihydro-1,4-benzodioxin-5-yl)piperazine and (2R)-2-[(tert-butoxycarbonyl)amino]-3-pyridin-4-ylpropanoic acid, according to the procedures outlined in examples 1, 2 and 3) (440 mg.; 1.2 mmol) in dichloromethane (5 mL), at 0° C., was added triethylamine (0.33 mL; 2.4 mmol), followed by a solution of 1-methyl-1-cyclohexanecarbonyl chloride (190 mg.; 1.2 mmol) in dichloromethane (1 mL). The reaction mixture was stirred while allowing to warm to ambient temperature over 1 hour, washed sequentially with saturated aqueous NaHCO$_3$ and brine, dried over MgSO$_4$, filtered, and the solvent removed in vacuo. Treatment with ethanolic HCl afforded the dihydrochloride salt, m.p. 188–190° C.; MS (+) ESI [M+H]$^+$ @ m/z 479; $^1$H NMR, 400 MHz, DMSO-d$_6$. Analysis for C$_{28}$H$_{38}$N$_4$O$_3$.2HC 11.5H$_2$O Calculated: C, 58.13; H, 7.49; N, 9.68 Found: C, 57.94; H, 7.83; N, 9.54

EXAMPLE 24

Cyclohexanecarboxylic acid {(1R)-2-[4-(2,3-dihydro-benzo[1,4]dioxin-5-yl)-piperazin-1-yl]-1-pyridin-3-ylmethyl-ethyl}-methyl-amide

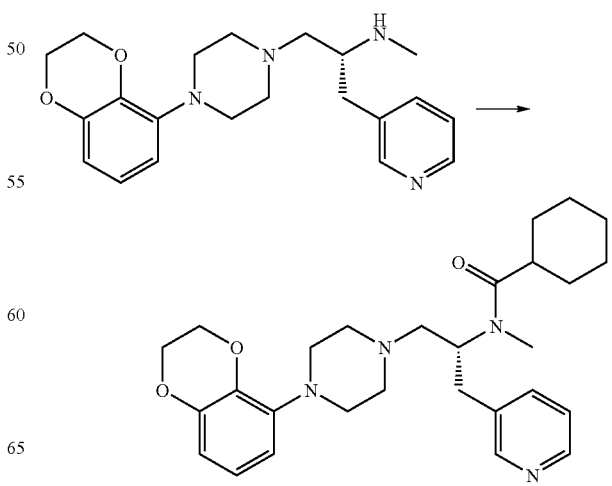

To a solution of (2R)-1-[4-(2,3-dihydro-1,4-benzodioxin-5-yl)piperazin-1-yl]-N-methyl-3-pyridin-3-ylpropan-2-amine (prepared in 4 steps from 1-(2,3-dihydro-1,4-benzodioxin-5-yl)piperazine and (2R)-2-[(tert-butoxycarbonyl)amino]-3-pyridin-3-ylpropanoic acid, according to the procedures outlined in examples 11, 12, 16 and 17) (200 mg.; 0.5 mmol) in dichloromethane (5 mL), at 0° C., was added triethylamine (0.14 mL; 1 mmol), followed by a solution of cyclohexanecarbonyl chloride (80 mg.; 0.5 mmol) in dichloromethane (1 mL). The reaction mixture was stirred while allowing to warm to ambient temperature over 1 hour, washed sequentially with saturated aqueous NaHCO$_3$ and brine, dried over MgSO$_4$, filtered, and the solvent removed in vacuo. Treatment with ethanolic HCl afforded the dihydrochloride salt, m.p. 167–170° C.; MS (+) ESI [M+H]$^+$ @ m/z 479; $^1$H NMR, 400 MHz, DMSO-d$_6$. Analysis for $C_{28}H_{38}N_4O_3 \cdot 2HCl \cdot 1.75H_2O$ Calculated: C, 58.68; H, 7.52; N, 9.61 Found: C, 57.33; H, 7.59; N, 9.54

EXAMPLE 25

Cyclohexanecarboxylic acid {(1R)-2-[4-(2,3-dihydro-benzo[1,4]dioxin-5-yl)-piperazin-1-yl]-1-pyridin-4-ylmethyl-ethyl}-methyl-amide

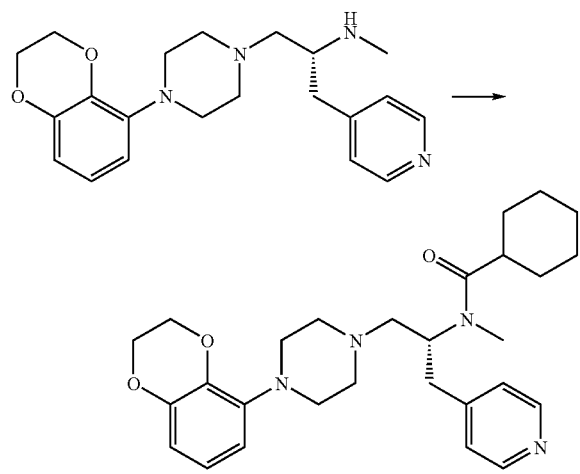

To a solution of (2R)-1-[4-(2,3-dihydro-1,4-benzodioxin-5-yl)piperazin-1-yl]-N-methyl-3-pyridin-4-ylpropan-2-amine (prepared in 4 steps from 1-(2,3-dihydro-1,4-benzodioxin-5-yl)piperazine and (2R)-2-[(tert-butoxycarbonyl)amino]-3-pyridin-4-ylpropanoic acid, according to the procedures outlined in examples 11, 12, 16 and 17) (280 mg.; 0.75 mmol) in dichloromethane (5 mL), at 0° C., was added triethylamine (0.21 mL; 1.5 mmol), followed by a solution of cyclohexanecarbonyl chloride (110 mg.; 0.75 mmol) in dichloromethane (1 mL). The reaction mixture was stirred while allowing to warm to ambient temperature over 1 hour, washed sequentially with saturated aqueous NaHCO$_3$ and brine, dried over MgSO$_4$, filtered, and the solvent removed in vacuo. Treatment with ethanolic HCl afforded the dihydrochloride salt, m.p. 167–170° C.; MS (+) ESI [M+H]$^+$ @ m/z 479; $^1$H NMR, 400 MHz, DMSO-d$_6$. Analysis for $C_{28}H_{38}N_4O_3 \cdot 2HCl \cdot 2H_2O$ Calculated: C, 57.24; H, 7.55; N, 9.53 Found: C, 56.42; H, 7.39; N, 9.24

Pharmacology

Affinity for the serotonin 5-HT$_{1A}$ receptor was established by assaying the test compound's ability to displace [$^3$H] 8-OHDPAT from its binding site on the receptor complex in CHO cells stably transfected with the human 5-HT$_{1A}$ receptor following the procedure described by J. Dunlop, Y. Zhang, D. Smith and L. Schechter (Eur. J. Pharmacol., submitted; variation of a procedure described by J. Zgombick et al., Naunyn-Schmiedeberg's Arch. Pharmacol., 354, 226–236 (1996)). The compounds of this invention displayed high affinity for the 5-HT$_{1A}$ receptor, as shown in Table 1.

Some of the compounds of this invention demonstrated partial agonist activity, as measured by their ability to reverse the stimulation of cyclic adenosinemonophosphate (cAMP) in CHO cells stably transfected with the human 5-HT$_{1A}$ receptor. EC$_{50}$ values are determined for the active test compounds. Stably transfected CHO cells were grown in DMEM containing 10% heat inactivated FBS and non-essential amino acids. The cells are plated at a density of ×10$^6$ cells per well in a 24 well plate and incubated for 2 days in a CO$_2$ incubator. On the second day, the media is replaced with 0.5 mL treatment buffer (DMEM+25 mM HEPES, 5 mM theophylline, 10 mM pargyline) and incubated for 10 minutes at 37° C. Wells are treated with forskolin (1 mM final concentration) followed immediately by the test compound (0.1 and 1 mM for initial screen) and incubated for an additional 10 minutes at 37° C. The reaction is terminated by removal of the media and addition of 0.5 mL ice cold assay buffer (supplied in the RIA kit). Plates are stored at −20° C. prior to assessment of cAMP formation by RIA. Selected compounds of this invention which demonstrated agonist or partial agonist activity in this assay are shown in Table 1.

Compounds shown to have no agonist activity (Emax=0%) are further analyzed to determine antagonist activity, as measured by the test compound's ability to inhibit forskolin-stimulated cAMP turnover in CHO cells stably transfected with the human 5-HT$_{1A}$ receptor using a procedure described by J. Dunlop, Y. Zhang, D. Smith and L. Schechter [Eur. J. Pharmacol., submitted; variation of a procedure described by J. Zgombick et al., Naunyn-Schmiedeberg's Arch. Pharmacol., 354, 226–236 (1996)]. Selected compounds of this invention which demonstrated 5-HT$_{1A}$ antagonist activity in this assay are shown in Table 1.

TABLE 1

| Example | 5-HT$_{1A}$ Affinity (IC$_{50}$) | Agonist Activity cAMP (EC$_{50}$) | Antagonist Activity cAMP (IC$_{50}$) |
|---|---|---|---|
| Example 4 | 0.48 nM | 20.54 nM | — |
| Example 5 | 0.88 nM | — | 13.2 nM |
| Example 9 | 0.56 nM | 141.5 nM | — |
| Example 10 | 0.72 nM | — | 11.3 nM |
| Example 14 | 1.26 nM | 53.0 nM | — |
| Example 15 | 0.74 nM | — | 4.5 nM |
| Example 18 | 3.00 nM | — | 132.5 nM |
| Example 22 | 2.58 nM | 10.2 nM | — |
| Example 23 | 1.13 nM | 108.24 | — |
| Example 24 | 2.48 nM | — | 77.0 nM |
| Example 25 | 3.81 nM | — | 115.0 nM |

Pharmaceutical Composition

Applicable solid carriers can include one or more substances which may also act as flavoring agents, lubricants, solubilizers, suspending agents, fillers, glidants, compression aids, binders or tablet-disintegrating agents or encapsulating materials. In powders, the carrier is a finely divided solid which is in admixture with the finely divided active ingredient. In tablets, the active ingredient is mixed with a carrier having the necessary compression properties in suitable proportions and compacted in the shape and size desired. The powders and tablets preferably contain up to 99% of the active ingredient. Suitable solid carriers include, for example, calcium phosphate, magnesium stearate, talc, sugars, lactose, dextrin, starch, gelatin, cellulose, methyl cellulose, sodium carboxymethyl cellulose, polyvinylpyrrolidine, low melting waxes and ion exchange resins.

Liquid carriers may be used in preparing solutions, suspensions, emulsions, syrups and elixirs. The active ingredient in this invention can be dissolved or suspended in a pharmaceutically acceptable liquid carrier such as water, an organic solvent, a mixture of both or pharmaceutically acceptable oils or fat. The liquid carrier can contain other suitable pharmaceutical additives such as solubilizers, emulsifiers, buffers, preservatives, sweeteners, flavoring agents, suspending agents, thickening agents, colors, viscosity regulators, stabilizers or osmo-regulators. Suitable examples of liquid carriers for oral and parenteral administration include water (particularly containing additives as above, e.g. cellulose derivatives, preferable sodium carboxymethyl cellulose solution), alcohols (including monohydric alcohols and polyhydric alcohols, e.g. glycols) and their derivatives, and oils (e.g. fractionated coconut oil and arachis oil). For parenteral administration the carrier can also be an oily ester such as ethyl oleate and isopropyl myristate. Sterile liquid carriers are used in sterile liquid form compositions for parenteral administration.

Liquid pharmaceutical compositions which are sterile solutions or suspensions can be utilized by, for example, intramuscular, intraperitoneal or subcutaneous injection. Sterile solutions can also be administered intravenously. Oral administration may be either liquid or solid composition form.

Preferably the pharmaceutical composition is in unit dosage form, e.g. as tablets or capsules. In such form, the composition is sub-divided in unit dose containing appropriate quantities of the active ingredient; the unit dosage forms can be packaged compositions, for example packeted powders, vials, ampoules, prefilled syringes or sachets containing liquids. The unit dosage form can be, for example, a capsule or tablet itself, or it can be the appropriate number of any such compositions in package form.

The dosage to be used in the treatment of a specific condition or disease must be subjectively determined by the attending physician. The variables involved include the specific condition or disease state and the size, age and response pattern of the patient.

Compounds and compositions of this invention may be used for treating a condition modulated by serotonin 5-$HT_{1A}$ receptors in the central nervous system and in the body of mammals. A method for effectively treating mammals suffering from such a condition comprises administration of a therapeutically effective amount of a compound of this invention. Conditions that may be treated using the compounds and method of this invention include, but are not limited to, depression, anxiety, impaired memory and/or learning resulting from neurodegenerative diseases such as Alzheimers disease, prostate cancer, nausea and vomiting.

Many variations of the present invention not illustrated herein will occur to those skilled in the art. The present invention is not limited to the embodiments illustrated and described herein, but encompasses all the subject matter within the scope of the appended claims

What is claimed is:
1. A compound according to the formula

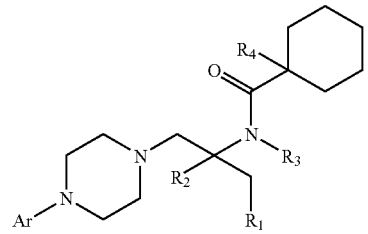

wherein:
Ar is selected from the group consisting of 2-methoxyphenyl, 1H-indol-4-yl and 2,3-dihydro-1,4-benzodioxin-5-yl;
$R_1$ is 2-, 3- or 4-pyridyl;
$R_2$ is H or $C_{1-6}$ alkyl;
$R_3$ is H or $C_{1-6}$ alkyl; and
$R_4$ is H or $C_{1-6}$ alkyl,
or an optical isomer thereof,
or a pharmaceutically acceptable salt of said compound or optical isomer thereof.

2. A compound according to claim 1 selected from the group consisting of:
(R)-1-Methyl-cyclohexanecarboxylic acid {2-[4-(2-methoxy-phenyl)-piperazin-1-yl]-1-pyridin-3-ylmethyl-ethyl}-amide;
(R)-Cyclohexanecarboxylic acid {2-[4-(2-methoxy-phenyl)-piperazin-1-yl]-1-pyridin-4-ylmethyl-ethyl}-amide;
(R)-1-Methyl-cyclohexanecarboxylic acid {2-[4-(2-methoxy-phenyl)-piperazin-1-yl]-1-pyridin-4-ylmethyl-ethyl}-amide;
(R)-1-Methyl-cyclohexanecarboxylic acid {2-[4-(2-methoxy-phenyl)-piperazin-1-yl]-1-pyridin-2-ylmethyl-ethyl}-amide;
(R)-Cyclohexanecarboxylic acid {2-[4-(2-methoxy-phenyl)-piperazin-1-yl]-1-pyridin-2-ylmethyl-ethyl}-amide;
1-Methyl-cyclohexanecarboxylic acid {(1R)-2-[4-(2-methoxy-phenyl)-piperazin-1-yl]-1-pyridin-2-ylmethyl-ethyl}-methyl-amide;
1-Methyl-cyclohexanecarboxylic acid {(1R)-2-[4-(1H-indol-4-yl)piperazin-1-yl]-1-pyridin-2-ylmethyl-ethyl}-methyl-amide;
1-Methyl-cyclohexanecarboxylic acid {(1R)-2-[4-(2,3-dihydro-benzo[1,4]dioxin-5-yl)-piperazin-1-yl]-1-pyridin-3-ylmethyl-ethyl}-amide;
1-Methyl-cyclohexanecarboxylic acid {(1R)-2-[4-(2,3-dihydro-benzo[1,4]dioxin-5-yl)-piperazin-1-yl]-1-pyridin-4-ylmethyl-ethyl}-amide;
Cyclohexanecarboxylic acid {(1R)-2-[4-(2,3-dihydro-benzo[1,4]dioxin-5-yl)-piperazin-1-yl]-1-pyridin-3-ylmethyl-ethyl}-methyl-amide;
Cyclohexanecarboxylic acid {(1R)-2-[4-(2,3-dihydro-benzo[1,4]dioxin-5-yl)-piperazin-1-yl]-1-pyridin-4-ylmethyl-ethyl}-methyl-amide;
and pharmaceutically acceptable salts thereof.

3. A compound according to claim 1 wherein:
$R_2$ is H;
$R_3$ is H, methyl or ethyl; and
$R_4$ is H or methyl,
or a pharmaceutically acceptable salt thereof.

4. A compound according to claim 3 having a chiral carbon center in the R configuration.

5. A method of treating a condition modulated by serotonin 5-HT$_{1A}$ receptors in the central nervous system and in the body of a mammal which method comprises administration, to a mammal having such a condition, of a therapeutically effective amount of a compound according to claim 1,
   wherein said condition is depression, anxiety, impaired memory resulting from Alzheimer's disease, impaired learning resulting from Alzheimer's disease, nausea, vomiting, or a combination thereof.

6. The method according to claim 5 wherein the condition is depression.

7. The method according to claim 5 wherein the condition is anxiety.

8. The method according to claim 5 wherein the condition is impaired memory resulting from Alzheimer's disease, impaired learning resulting from Alzheimer's disease, or a combination thereof.

9. The method according to claim 5 wherein the condition is nausea and vomiting.

10. A pharmaceutical composition which comprises a pharmaceutically acceptable carrier and a therapeutically effective amount of a compound of claim 1.

11. A composition according to claim 10 wherein said compound consists essentially of an optical isomer having a chiral carbon center in the R configuration.

* * * * *